(12) United States Patent
Diccianni et al.

(10) Patent No.: US 6,207,119 B1
(45) Date of Patent: Mar. 27, 2001

(54) SEALED SYSTEM FOR HANDLING, MANIPULATING AND FORMULATING MATERIALS IN AN ISOLATED ENVIRONMENT

(76) Inventors: Anthony Michael Diccianni, 330 Knoll Rd., Norristown, PA (US) 19401; Eric Anthony Diccianni, 200 Signal Hill Ct., North Wales, PA (US) 19454

(*) Notice: Subject to any disclaimer, the term of this patent is extended or adjusted under 35 U.S.C. 154(b) by 0 days.

(21) Appl. No.: 08/232,565

(22) Filed: Apr. 25, 1994

(51) Int. Cl.[7] .................................................. A61L 2/00
(52) U.S. Cl. .......................... 422/295; 312/1; 312/242; 422/120; 422/297; 422/300; 454/57
(58) Field of Search ........................... 422/295, 297, 422/300, 120; 312/1, 242; 454/57, 56, 49–52

(56) References Cited

U.S. PATENT DOCUMENTS

| | | | |
|---|---|---|---|
| 3,380,219 | 4/1968 | Madl, Jr. ............................. | 52/664 |
| 3,486,311 | 12/1969 | Allan, Jr. ............................ | 55/355 |
| 3,774,522 | 11/1973 | Marsh ................................. | 98/33 R |
| 4,015,495 | * 4/1977 | Andersson et al. ................. | 422/297 |
| 4,643,627 | 2/1987 | Bednorz et al. .................... | 414/217 |
| 4,667,579 | 5/1987 | Daw ................................... | 98/33.1 |
| 4,670,227 | * 6/1987 | Smith ................................. | 422/297 |
| 4,706,551 | 11/1987 | Schofield ........................... | 98/1 |
| 4,765,810 | 8/1988 | Wetzel ............................... | 55/270 |
| 4,795,300 | 1/1989 | Tomaselli et al. ................. | 414/217 |
| 4,819,549 | 4/1989 | Gillingham et al. ............... | 98/1 |
| 4,883,511 | 11/1989 | Gustin et al. ...................... | 55/355 |
| 4,883,513 | 11/1989 | Monson et al. .................... | 55/385.2 |
| 4,920,768 | * 5/1990 | Cares et al. ........................ | 312/1 X |
| 4,946,484 | 8/1990 | Monson et al. .................... | 55/385.2 |
| 4,971,774 | * 11/1990 | Schwanke et al. ................ | 422/295 X |
| 5,062,758 | 11/1991 | Trillwood ........................... | 414/217 |
| 5,139,318 | * 8/1992 | Broxup .............................. | 312/1 |
| 5,169,217 | * 12/1992 | Orchard et al. .................... | 312/1 X |
| 5,257,957 | 11/1993 | Diccianni et al. .................. | 454/57 |

FOREIGN PATENT DOCUMENTS

| | | | |
|---|---|---|---|
| 95971 | * 12/1983 | (EP) ................................... | 422/295 |

OTHER PUBLICATIONS

English–language translation of European Patent Document No. 0 095 971, dated Dec. 7, 1983 (without drawings).

* cited by examiner

Primary Examiner—Krisanne Thornton
(74) Attorney, Agent, or Firm—Akin, Gump, Strauss, Hauer & Feld, L.L.P.

(57) ABSTRACT

A sealed system for handling, manipulating and formulating materials in an isolated environment which includes an isolation system for performing operations on the materials, an accessory for receiving, performing a procedure, and providing items, and a sealing device interconnecting the isolation system and the accessory. The isolation system has an interior at least partially defined by a plurality of walls and a transfer port positioned on one of the walls for transferring items into and out of the isolation system. The accessory is selectively coupled to the transfer port and has an interior accessed by an opening. The sealing device includes a trough of predetermined configuration and a blade of corresponding configuration. The trough has a sealing substance disposed therein, and the blade and the trough each surround one of the transfer port and the opening. The blade is sealingly mounted to a mounting member which is sealingly mounted to the accessory to seal the interior of the accessory. When the blade is placed within the trough and sealingly engages the sealing substance, external matter is prevented from passing into the interiors through the transfer port and the opening and the coupled accessory is accessible from the isolation system.

20 Claims, 4 Drawing Sheets

SEALED SYSTEM FOR HANDLING, MANIPULATING AND FORMULATING MATERIALS IN AN ISOLATED ENVIRONMENT

FIELD OF THE INVENTION

The present invention relates to a sealed system for handling, manipulating and formulating materials in an isolated environment and, more particularly, to an isolation system or facility interfaced to an accessory by way of an interfacing assembly to form the sealed system.

BACKGROUND OF THE INVENTION

In many industrial areas including pharmaceuticals, electronics, chemicals, and others, a significant amount of experimentation, manufacturing, production, and the like must be performed in sterile, contaminant-free, germ-free, and/or particle-free work spaces, often referred to as clean rooms. Additionally, special work spaces are necessary in order to isolate potentially harmful environments due to the presence of dangerous chemicals and/or biological matter. However, the cost to build, maintain, and operate such work spaces is significant. For example, special air filtering equipment must be provided for the work space, persons entering and leaving the work space must be specially attired and must observe strict transmitting rules, and materials must be exchanged into and out of the work space without allowing contaminants to be exchanged. As may be understood, the cost of providing such a work space is considerable and is ultimately passed on from the industry to customers and consumers.

As may be recognized, the biggest source of contamination in connection with a work space is caused by people entering and leaving the work space. Accordingly, one way the aforementioned industries are attempting to reduce costs is to remove the people from the work space. Thus, in the handling, manipulating and formulating of hazardous, toxic or other materials in a clean environment, it is known to employ sealed enclosures, locally controlled environments, isolation systems, and the like to allow at least one operator to work on materials in the interior of the enclosure without physically exposing the operator and the interior to one another.

In order to allow an operator to perform tasks in the interior of the sealed enclosure, the operator may reach in through one or more glove ports positioned on the enclosure. In relatively large sealed enclosures, the operator may employ a protective upper torso suit. Such a facility for providing a sealed work area is described more thoroughly in U.S. Pat. No. 5,257,957, hereby incorporated by reference.

While such facilities, locally controlled environments, sealed enclosures, isolation systems, and the like have been known for some time, the cleaning and sterilization of materials in the interior of the sealed enclosure has been problematic. In a typical clean room, an autoclave or the like is normally provided as an instrument for cleaning and sterilizing materials within the clean room. Accordingly, a properly garbed operator in the clean room would clean and sterilize a part or instrument by inserting the part or instrument into the autoclave and then operating the autoclave. Thereafter, the cleaned and sterilized part or instrument would be removed from the autoclave and used in the clean room.

Typically, an autoclave is a relatively large, heavy instrument and can occupy up to about 150 cubic feet of space. Also, and as is well known, an autoclave employs high pressure steam to clean and sterilize instruments. Accordingly, the autoclave is preferably positioned in a cavity within a masonry wall such that the autoclave is properly supported and such that damage from a sudden release of pressure is minimized.

Referring now to a facility such as that disclosed in U.S. Pat. No. 5,257,957, it should be apparent that the use of an autoclave in connection with the facility such that the autoclave is accessible from the interior of the facility presents several problems. Although the autoclave could be placed in the interior of the facility, the space occupied by the autoclave and the weight of the autoclave would be excessive. Further, the facility would not typically provide the same shielding as if the autoclave were placed within a masonry wall. As will also be recognized, the maintenance, cleaning and repair of the autoclave is complicated when the autoclave is located in the interior of the facility. Therefore, a need has arisen for a means and a method for coupling an isolation system for handling, manipulating and formulating materials and an autoclave positioned exterior to the isolation system, while maintaining the controlled environment within the isolation system.

SUMMARY OF THE INVENTION

Briefly stated, the present invention comprises a sealed system for handling, manipulating and formulating materials in an isolated environment. The system includes an isolation system for performing at least a portion of handling, manipulating, and formulating the materials. The isolation system has an interior at least partially defined by a plurality of walls, an inlet port for allowing air to flow into the interior, an outlet port for allowing air to flow out of the interior, and a transfer port positioned on one of the walls for transferring items into and out of the isolation system. An accessory receives and provides the transferred items and performs a procedure on the items. The accessory is selectively coupled to the transfer port of the isolation system and has an interior for receiving the items. The interior is accessible through an opening. A generally outwardly extending trough of predetermined configuration surrounds one of the transfer port of the isolation system and the opening of the accessory. The trough has a sealing substance disposed therein. A generally outwardly extending blade of predetermined configuration surrounds the other of the transfer port of the isolation system and the opening of the accessory. The configuration of the blade corresponds to the configuration of the trough. The blade is aligned with and placed within the trough such that the blade sealingly engages the sealing substance within the trough to prevent external matter from passing into the interior of the isolation system and the interior of the accessory through the transfer port and the opening such that the interior of the coupled accessory is accessible from the interior of the isolation system through the transfer port of the isolation system and the opening of the accessory.

In another aspect, the present invention is directed to a sealed system for handling, manipulating and formulating materials in an isolated environment. The system includes an isolation system for performing at least a portion of the handling, manipulating, and formulating of the materials. The isolation system has an interior at least partially defined by a plurality of walls, an inlet port for allowing air to flow into the interior, an outlet port for allowing air to flow out of the interior, and a transfer port positioned on one of the walls for transferring items into and out of the isolation system. The isolation system is portable. An autoclave receives the items from the isolation system, sterilizes the items, and returns the items to the isolation system. The autoclave is selectively coupled to the transfer port of the isolation system and has an interior for accepting the items. The interior is accessible through an opening. The opening and transfer port are in registry when the autoclave is coupled with the isolation system. A sealing device interconnects the isolation system and the autoclave and sealingly engages the transfer port of the isolation system to the opening of the autoclave to prevent external matter from passing into the interior of the isolation system and the interior of the autoclave through the transfer port and the opening.

In another aspect, the present invention is directed to a method for sealingly coupling an isolation system for handling, manipulating and formulating materials and an accessory for receiving items transferred from and providing items transferred to the isolation system. The isolation system has an interior at least partially defined by a plurality of walls and a transfer port positioned on one of the walls. The accessory has an interior accessible through an opening. The method comprises the steps of positioning the isolation system with respect to the accessory such that the transfer port and the opening are proximate one another and in registry and sealingly coupling the transfer port to the opening to prevent external matter from passing into the isolation system and the accessory through the transfer port and the opening such that the interior of the coupled accessory is accessible from the interior of the isolation system through the transfer port and the opening.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF PREFERRED EMBODIMENTS

Certain terminology may be used in the following description for convenience only and is not limiting. The words "left", "right", "upper" and "lower" designate directions in the drawings to which reference is made. The words "inwardly" and "outwardly" refer to directions toward and away from, respectively, the geometric center of a referenced element. The terminology includes the words above specifically mentioned, derivatives thereof, and words of similar import.

Figure 1:
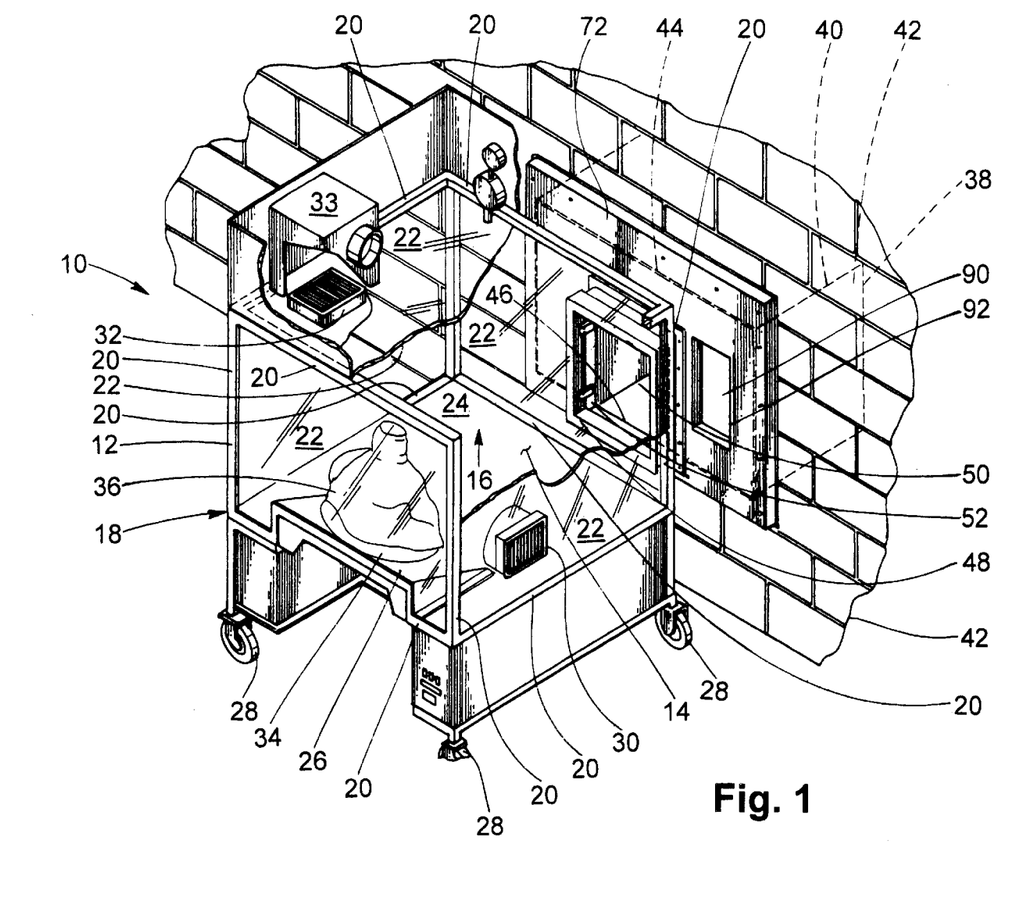
FIG. 1 is a perspective view of a sealed system for handling, manipulating and formulating materials in an isolated environment in accordance with the present invention.

Referring to the drawings in detail, wherein like numerals are used to indicate like elements throughout, there is shown in FIG. 1 a sealed system for handling, manipulating and formulating materials in an isolated environment. As seen, the sealed system includes a facility, sealed enclosure, locally controlled environment, or isolation system 10 for providing a sealed work area 16 to handle, manipulate and formulate materials (not shown). The facility 10 comprises a walled enclosure 12 having an interior periphery 14 defining the work area 16. The enclosure 12 consists of a frame 18 of tubular members 20 which are assembled together to provide a generally rigid structure. Preferably, the tubular members 20 may be welded, bolted and/or otherwise attached to form a generally parallelepiped shape.

Preferably, four generally vertically oriented panels 22 extend between the vertically extending tubular members 20 to form the sidewalls of the enclosure 12 and a single horizontally oriented panel 24 extends between the upper tubular members 20 to form the ceiling of the enclosure 12. Preferably, the panels 22 comprise a generally rigid transparent material for providing the enclosure 12 with a degree of structural integrity and to allow external observation of the interior of the enclosure 12. Such a transparent material may include plexiglass, polycarbonate, or rigid acrylic, although it is understood by one skilled in the art that other materials could be used to construct the panels 22, including glass or other transparent, generally rigid materials. Preferably, each of the panels 22 is sealingly coupled to the adjacent tubular members 20 such that the atmosphere internal and external to the facility 10 does not pass therebetween.

Extending between the lower tubular members 20 is a work panel 24 for providing a work surface. Preferably, the work panel 24 comprises a high-strength, lightweight metallic material such as stainless steel and is welded to each of the lower tubular members 20. However, one skilled in the art will recognize that the work panel 24 may be constructed of other high-strength, lightweight materials, such as aluminum or polyvinylchloride, without departing from the spirit and scope of the present invention. The work panel 24 includes a pulpit area 26 for allowing an operator to access the work area 16, as will be described below. Preferably, the work panel 24 is sealingly coupled to the adjacent tubular members 20 such that the atmosphere internal and external to the facility 10 does not pass therebetween.

Preferably, the facility 10 is portable. Accordingly, each of the vertically extending members 20 has a wheel 28 associated therewith for providing the enclosure 12 with a degree of portability.

The enclosure 12 may include at least one inlet port 30 for allowing air to flow into the enclosure work area 16 and at least one outlet port 32 for allowing air to flow out of the enclosure work area 16. Preferably, the inlet port 30 and the outlet port 32 each receive a high efficiency particulate air (HEPA) filter (not shown) or the like for filtering the air. Flow control means 33 such as a fan or a blower are provided to cause air to flow from the inlet port 30 through the interior periphery 14 of the facility 10 to the outlet port 32.

The enclosure 12 includes worker access means for allowing a portion of a worker (not shown) to access the enclosure work area 16. Preferably, the worker access means comprises a worker access port 34 located in the pulpit area 26 of the work panel 24. Also preferably, the worker access means further comprises suit means positioned within the work area 16 in sealed engagement with the worker access port 34 for permitting a worker to access the work area 16 without being exposed thereto. Preferably, the suit means comprises an upper-torso protective suit 36, as is understood by one skilled in the art.

Preferably, the facility 10 has a transfer port 48 positioned on one of the panels 22 to allow items (not shown) to be transferred into and out of the facility 10, as described in more detail hereinafter. Although not shown, the transfer port 48 may include a sealable hatch for sealing the transfer port 48 and maintaining the isolated environment of the facility 10.

The foregoing description of the facility 10 is brief because the facility 10 is well understood by those of ordinary skill in the art. For a more detailed discussion of the facility 10, attention is directed to the aforementioned U.S. Pat. No. 5,257,957.

Figure 2:
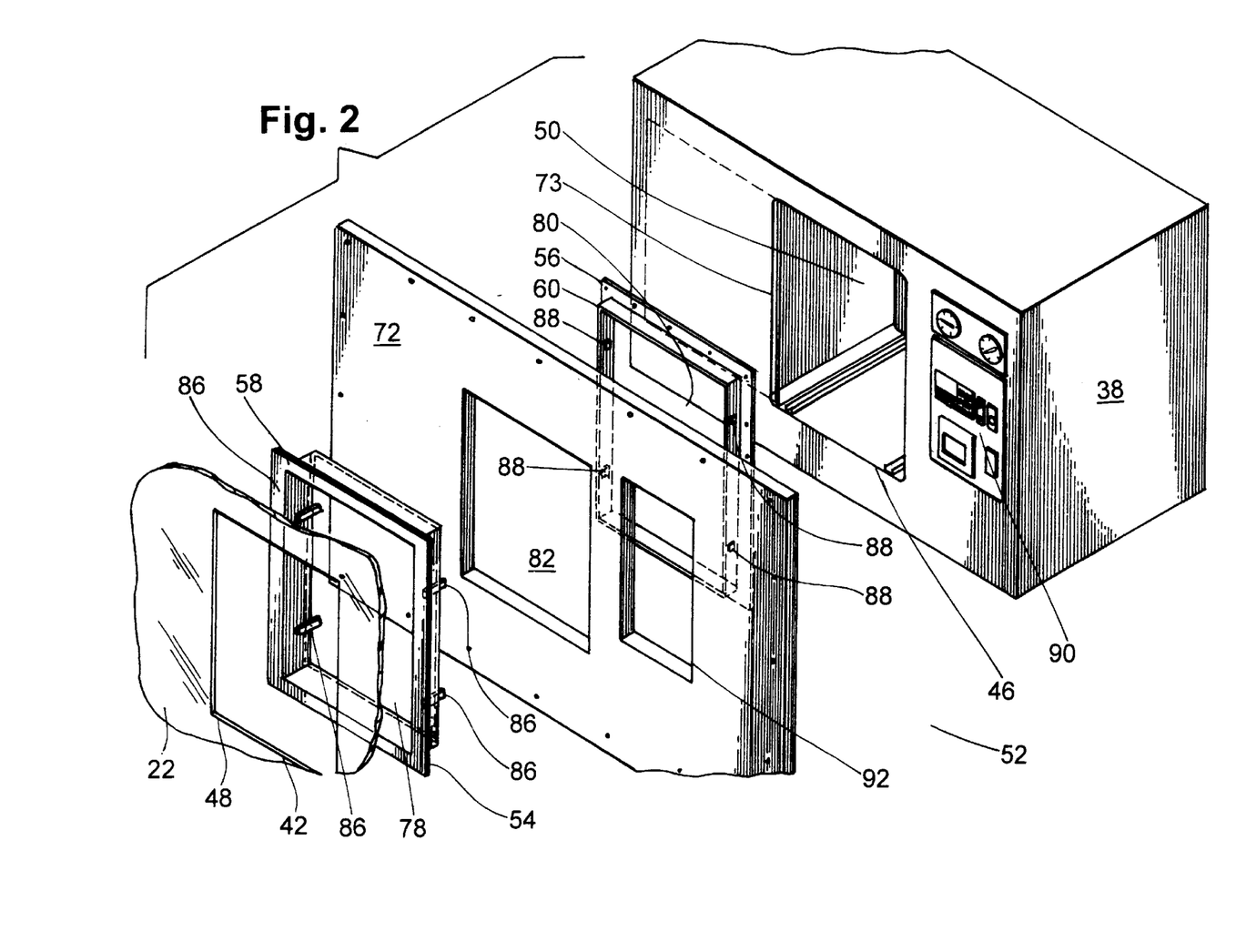
FIG. 2 is an enlarged exploded perspective view of an interfacing assembly and autoclave of the sealed system shown in FIG. 1.

Referring now to FIGS. 1 and 2, the sealed system includes means for interfacing the facility 10 to an accessory device. In the present embodiment, it is preferred that the accessory device be an autoclave 38. As will be recognized, the autoclave 38 receives parts, materials, instruments, and the like, and cleans and sterilizes the received items via super-heated high pressure steam. Preferably, the autoclave 38 is fixedly positioned within a cavity 40 in a wall 42 of a building. Also preferably, the wall 42 has an opening 44 in registry with an opening 46 of the autoclave 38.

In order that the autoclave 38 may receive items from the facility 10, sterilize the items, and return the items to the facility 10, the autoclave 38 is preferably selectively coupled to the transfer port 48 of the facility 10 and has an interior 50 for accepting the items. Preferably, the interior 50 is accessible through the opening 46 of the autoclave 38. Also preferably, the opening 46 of the autoclave 38 and the transfer port 48 of the facility 10 are in registry when the autoclave 38 is coupled to the facility 10.

As seen, a sealing device 52 is provided in order to sealingly couple the facility 10 to the autoclave 38. Preferably, the sealing device 52 prevents external matter from passing into the interior periphery 14 of the facility 10 and the interior 50 of the autoclave 38 through the transfer port 48 of the facility 10 and the opening 46 of the autoclave 38. As used herein external matter means ambient air or other gases, liquids, and solids external to the sealed system. As seen in FIG. 2, the sealing device 52 includes a female sealing member 54 and a male sealing member 56 for being accepted by the female sealing member 54.

Figure 3:
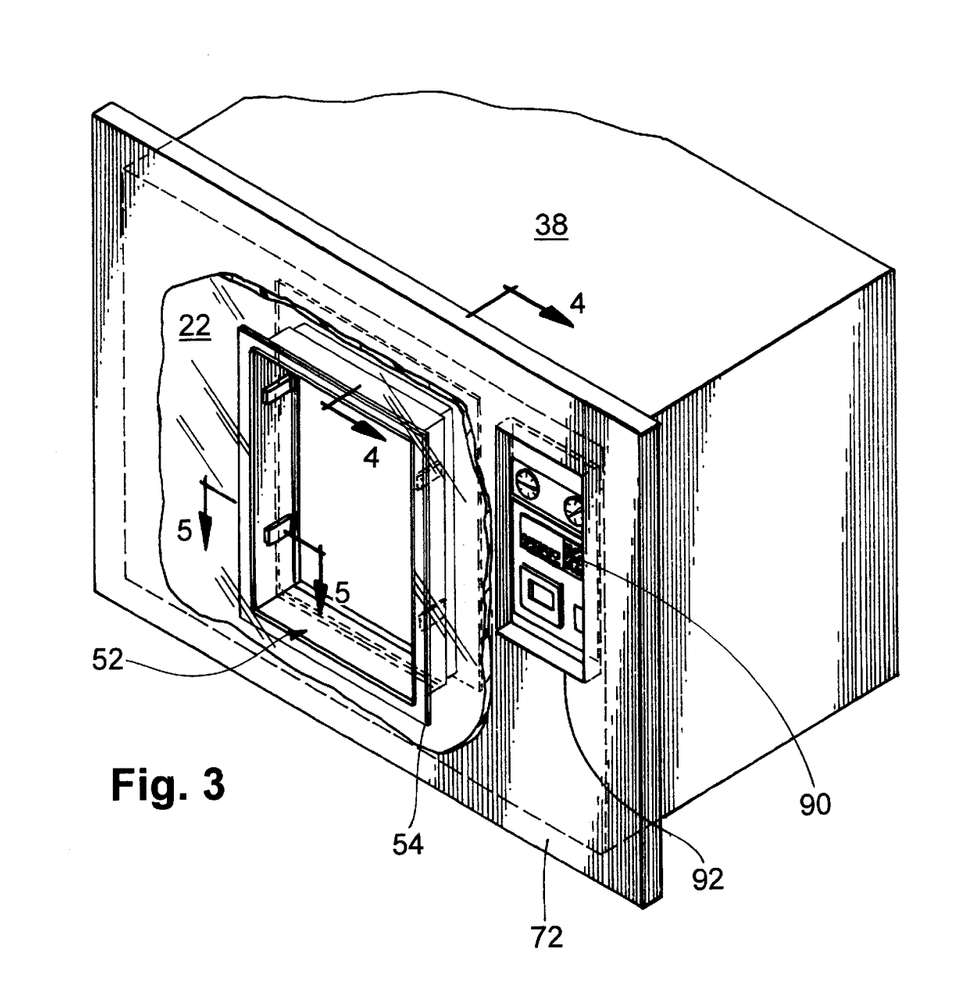
FIG. 3 is an enlarged perspective view of a portion of the sealed system showing the interfacing assembly and the autoclave.
Figure 4:
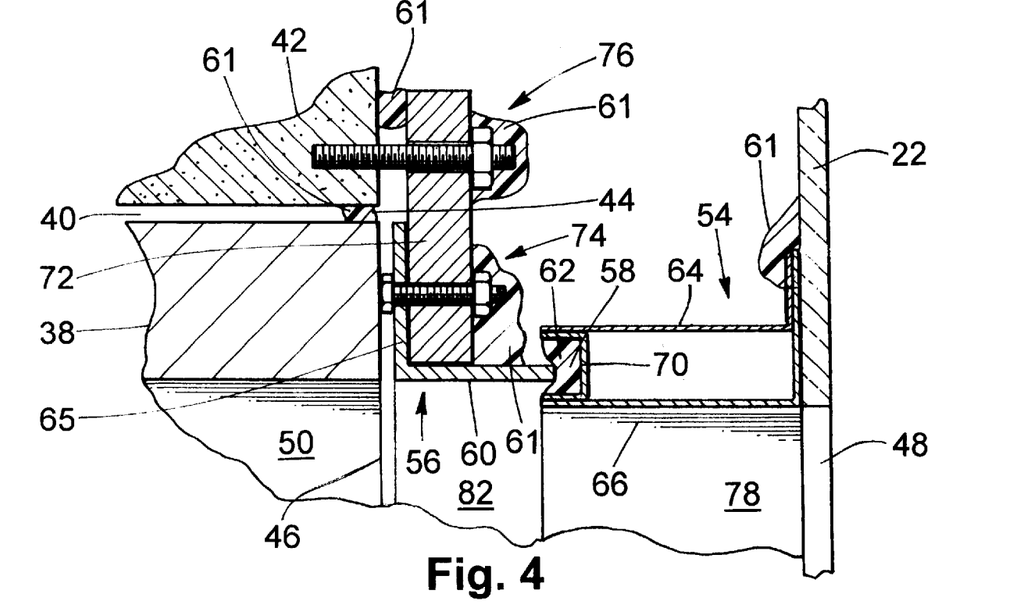
FIGS. 4 and 5 are greatly enlarged cross-sectional views of a portion of the interfacing assembly taken along lines 4—4 and 5—5, respectively, of FIG. 3.
Figure 5:
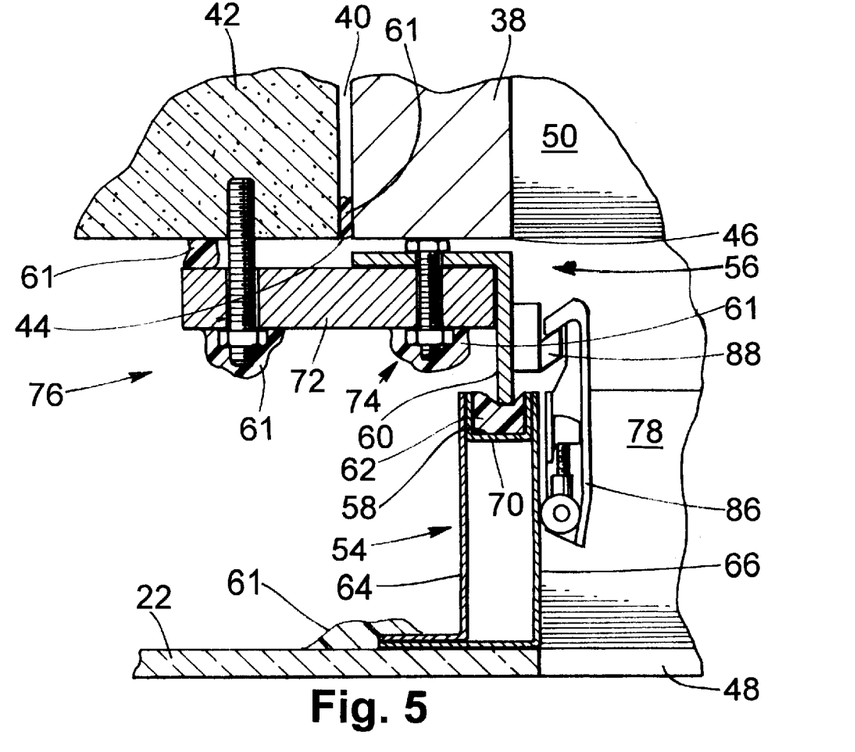

Preferably, and as best seen in FIGS. 4 and 5, the female sealing member 54 comprises a generally outwardly extending trough 58 and the male sealing member 56 comprises a generally outwardly extending blade 60. As best seen in FIGS. 2 and 3, the trough 58 has a predetermined configuration, is sealingly mounted to the facility 10 via the female sealing member 54, and surrounds the transfer port 48 of the facility 10. As also best seen in FIGS. 2 and 3 the blade 60 has a predetermined configuration, is sealingly mounted to the autoclave 38 via the male sealing member 56, and surrounds the opening 46 of the autoclave 38.

Preferably, the configuration of the blade 60 corresponds to the configuration of the trough 58. Also preferably, the trough 58 has a sealing substance 62 (seen in FIGS. 4 and 5) disposed therein. Thus, the sealingly mounted blade 60 may be aligned with and placed within the sealingly mounted trough 58 such that the blade 60 sealingly engages the sealing substance 62 within the trough 58 to prevent external matter from passing therebetween. With the mounted blade 60 and the mounted trough 58 thus combined, the interior 50 of the coupled autoclave 38 may be accessed from the interior periphery 14 of the facility 10 by the transfer port 48 of the facility 10 and the opening 46 of the autoclave 38.

Referring again to FIGS. 4 and 5, it is seen that the female sealing member 54 preferably comprises first and second generally L-shaped in cross section angle frames 64, 66 surrounding the transfer port 48 of the facility 10. One leg of the first L-shaped angle frame 64 is secured in facing engagement to one leg of the second L-shaped angle frame 66. The other legs of the first and second L-shaped angle frames 64, 66 are spaced from each other to define the trough 58. As best seen in FIG. 2, the female sealing member 54 surrounds and defines an inner area 78. To support the sealing substance 62 a distance outwardly from the panel 22, a generally U-shaped in cross section seat 70 is complementarily provided between the distal ends of the other legs of the first and second L-shaped angle frames 64, 66. The first and second L-shaped angle frames 64, 66 and the seat 70 are preferably constructed of a high strength light weight material, such as stainless steel, and preferably welded together. However, it is understood by those of ordinary skill in the art that the first and second L-shaped angle frames 64, 66 and seat 70 could be constructed of other materials and manufactured using different methods. For instance, the female member 54 could be constructed of a polymeric material and be molded as a single piece.

The female sealing member 54 is sealingly mounted to the facility 10 via the panel 22 in which the transfer port 48 is located, as seen in FIGS. 4 and 5. While any of a plurality of means may be employed to mount the female sealing member 54 to the panel 22, in the present embodiment it is preferred that the female sealing member be epoxied directly to the panel 22 and a bead of sealant material 61, such as silicone, be provided between the female sealing member 54 and the panel 22. Other mounting means include, for example, a plurality of nuts and bolts or the like (not shown) employed between the female sealing member 54 and the panel 22.

As also seen in FIGS. 4 and 5, the male sealing member 56 preferably comprises a generally L-shaped angle frame 65 surrounding the opening 46 of the autoclave 38. The outwardly extending leg of the angle frame 65 forms the blade 60. As best seen in FIGS. 2 and 3, the male sealing member 56 surrounds and defines an inner area 80. Preferably, the male sealing member 56 is constructed from the same material as the female sealing member 54.

It is understood by those of ordinary skill in the art that the present invention is not limited to mounting the male sealing member 56 on the autoclave 38 and the female sealing member 54 on the panel 22 and that the male sealing member 56 could be mounted on the panel 22 and the female sealing member 54 could be mounted on the autoclave 38. Further, other sealing devices could be used to sealingly connect the autoclave 38 and facility 10 without departing from the spirit and scope of the invention.

The male sealing member 56 is preferably sealingly mounted to the autoclave by way of a mounting member or bio-seal 72 having a predetermined thickness. Preferably, the blade 60 extends at least partially through the bio-seal 72, as described in more detail below, and the trough 58 extends a sufficient distance from the panel 22 to contact the blade 60. The male sealing member 56 may be sealingly mounted to the bio-seal 72 by any of a plurality of mounting means, although it is preferable that a plurality of nuts and bolts 74 be employed. However, one skilled in the art will recognize that other mounting means may be employed.

The bio-seal 72 has an aperture 82 in registration with the inner areas 78, 80 of the female and male sealing members 54, 56, the opening 46 of the autoclave 38, and the transfer port 48 of the facility 10. The aperture 82 is sized to complementarily receive the blade 60 of the male member 56, as best shown in FIGS. 4 and 5.

Preferably, the bio-seal or mounting member 72 is a generally planar sheet of high strength light weight material, such as stainless steel. One skilled in the art will recognize, however, that other suitable materials may be employed, such as aluminum, brass and polymeric materials.

Preferably, the bio-seal 72 with the mounted male member 56 is mounted to the exterior of the wall 42 having the cavity 40 within which the autoclave 38 is placed such that the bio-seal 72 entirely covers the opening 44 of the wall 42 and the inner area 80, aperture 82 and opening 46 of the autoclave 38 are aligned or in registry. Preferably, and as seen in FIGS. 4 and 5, a plurality of nuts and bolts 76 are employed to mount the bio-seal 72 to the wall 42. However, and again, one skilled in the art, from this disclosure, will recognize that other mounting means may be employed.

Preferably, a bead of a sealing compound or material 61, such as silicone, is applied where the female sealing member 54 meets the panel 22, where the male sealing member 56 meets the bio-seal 72, where the bio-seal meets the wall 42, where the wall 42 meets the autoclave 38 and over the nuts and bolts 74, 76. Thus, external matter is prevented from passing into the interior 50 of the autoclave 38 and the interior periphery 14 of the facility 10 via any of the aforementioned meeting points. It is understood by those of ordinary skill in the art that the sealing bead may comprise any of several well-known sealing materials, including sealing caulks and gels.

Preferably, the sealing substance 62 within the trough 58 is a gel. As one skilled in the art will recognize, any of several gel sealing substances may be employed so long as the gel sealing substance provides a tight seal with the blade 60 when the blade 60 is inserted within the trough 58. Preferably, the female and male sealing members 54, 56 are pre-formed and pre-matched, the female sealing member 56 is pre-loaded with the sealing substance 62, and the complete sealing device 52 is supplied as a single package. Accordingly, the female sealing member 54 is assured of properly mating with the male seal member 56.

With the female sealing member 54 sealingly mounted to the facility 10 at the transfer port 48, external matter may not pass into the interior periphery 14 of the facility 10 except by the transfer port 48. Similarly, with the male sealing member 56 sealingly mounted to the bio-seal 72, with the bio-seal 72 sealingly mounted to the wall 42 having the autoclave 38, and with the wall 42 sealed to the autoclave 38, external matter may not pass into the interior 50 of the autoclave 38 except by the opening 46 of the autoclave 38.

With the female sealing member 54 of the sealing device 52 sealingly mounted to the facility 10 and with the male sealing member 56 of the sealing device 52 sealingly mounted to the autoclave 38, the facility 10 is sealingly coupled to the autoclave 38 in the following manner. Preliminarily, the facility 10 must be positioned with respect to the autoclave 38 such that the transfer port 48 and the opening 46 of the autoclave 38 are proximate one another. More particularly, the female sealing member 54 and the male sealing member 56 must be aligned in order to be in registry. In order to position the facility 10 as such, the facility 10 is preferably moved on a flooring surface (not shown) adjacent the wall 42 by way of the wheels 28 on the facility 10.

It may also be necessary to raise or lower the facility 10 in order to achieve alignment and registry. If so, the facility 10 may comprise any of a plurality of vertical adjusting means (not shown). As one skilled in the art will recognize, the vertical adjusting means may include one or more jacking devices, hydraulic devices, or other suitable means for vertically adjusting the facility 10.

Once the female and male sealing members 54, 56 are aligned and in registry, the blade 60 of the male sealing member 56 is placed within the trough 58 of the female sealing member 54, and the blade 60 is sealingly engaged to the sealing substance 62 within the trough 58. With the male sealing member 56 sealingly coupled to the female sealing member 54, external matter is prevented from passing into the interior periphery 14 of the facility 10 and the interior 50 of the autoclave 38 via the transfer port 48 of the facility 10 or the opening 46 of the autoclave 38. Further, with the male sealing member 56 sealingly coupled to the female sealing member 54 as such, the interior 50 of the autoclave 38 is accessible from the interior periphery 14 of the facility 10 through the transfer port 48 of the facility 10 and the opening 46 of the autoclave 38.

Preferably, and as best seen in FIG. 5, a releasable securing means is provided to maintain the blade 60 in sealing engagement with the trough 58 and the sealing substance 62 therein. As seen in FIGS. 2 and 3, the securing means may comprise a plurality of first securing members 86 spaced around the trough 58 of the female sealing member 54 at the inner area 78 and a corresponding plurality of complementary second securing members 88 spaced around the blade 60 of the male sealing member 56 at the inner area 80. As arranged in the Figures, an operator in the torso suit 36 may reach from the interior periphery 14 of the facility 10 and through the transfer port 48 to couple and uncouple the first and second members 86, 88 of the releasable securing means.

Referring again to FIG. 5, in the present embodiment the first and second securing members 86, 88 preferably comprise a conventional latch and a latch keeper, well understood by those of ordinary skill in the art. However, one skilled in the art will also recognize that any of several other well-known releasable securing means may be employed, such as nuts and bolts. While it is preferred that the releasable securing means be positioned within the sealing device 52 to prevent tampering, it is understood by those of ordinary skill in the art that the releasable securing devices could mounted on the exterior of the sealing device 52.

With the releasable securing means, the female and male sealing members 54, 56 may be disengaged from one another in order to separate the facility 10 from the autoclave 38 for cleaning, maintenance and other purposes. When the female and male sealing members 54, 56 are to be again engaged, the sealing substance 62 is self-sealing and reusable and does not have to be replenished. Accordingly, the blade 60 when placed within the trough 58 will sealingly engage to sealing substance 62 over and over again. However, the sealing substance 62 may degrade after a number of connections and disconnections, in which case the sealing substance 62 is merely replenished.

In order to sterilize and clean parts, materials, and instruments from within the facility 10, an operator typically would reach through the transfer port 48, the inner areas 78, 80 of the respective female and male sealing members 54, 56, the aperture 82 of the bio-seal 72, and the opening 46 of the autoclave 38 to place the parts, materials, and/or instruments within the autoclave 38. Thereafter, a horizontally slidable door 73 (shown only in FIG. 2) is closed to seal the opening 46 of the autoclave 38. However, it is understood by those of ordinary skill in the art that the door 73 may be a hinged door opening outwardly from the autoclave 38 or a vertically slidable door mounted to the autoclave 38. However, one skilled in the art will recognize that a plurality of other types of doors may be employed without departing from the spirit and scope of the invention.

With the autoclave 38 sealed via the door 73, a control panel 90 (as seen in FIGS. 1–3) on the autoclave 38 is accessed to operate the autoclave 38. The operation of autoclaves via control panels is well known in the art and, therefore, further discussion in this regard is unnecessary. Preferably, the bio-seal 72 has an aperture 92 for allowing access to the control panel 90 through the bio-seal 72. Also preferably, a sealing bead (not shown) is applied about the periphery of the aperture 92 where the bio-seal 72 meets the autoclave 38 such that external matter is not permitted to pass behind the bio-seal 72 and into the interior 50 of the autoclave 38 and the interior periphery 14 of the facility 10.

In order to provide accessibility to the control panel 90, the sealed system may have any of several different arrangements. In a first arrangement, and as shown in FIG. 1, the transfer port 48 is positioned on the facility 10 such that the coupled facility 10 does not directly block the control panel 90 and the space directly in front of the control panel 90 is free. Accordingly, the control panel 10 is externally accessible by an operator.

In a second arrangement (not shown), the transfer port 48 of the facility 10 is positioned on the facility 10 to place the coupled facility 10 directly in front of the control panel 92. However, the female and male sealing members 54, 56 are constructed to extend outwardly a sufficient distance from the facility 10 and autoclave 38, respectively, to allow an operator to reach between the facility 10 and the autoclave 38 to access the control panel 90.

In a third arrangement (not shown), the control panel 90 is separate from the autoclave 38 yet electrically interconnected thereto. As such, the control panel 90 could be placed internal or external to the facility 10 in a plurality of appropriate positions via appropriate means.

In a fourth arrangement (not shown), a second set of female and male sealing members are mounted to surround the control panel 90 and a control panel access port on the facility 10 in a manner consistent with the female and male sealing members 54, 56. As a result, the control panel 90 is directly accessible from the interior periphery 14 of the facility 10.

In a fifth arrangement (not shown), the female and male sealing members 54, 56, the transfer port 48 of the facility 10, and the aperture 82 in the bio-seal 72 are sized to surround both the opening 46 and the control panel 90 of the autoclave 38.

It is understood by those of ordinary skill in the art from this disclosure that the present invention is not limited to coupling the facility 10 to the autoclave 38 and that other facilities such as glove boxes or hard or soft walled isolation systems could be coupled to the autoclave 38 and that other accessories could be sealingly coupled to the facility 10, such as a freeze dry oven and lyophilizer without departing from the spirit and scope of the invention.

From the foregoing description, it can be seen that the present invention comprises a new and useful sealed system for handling, manipulating and formulating materials in an isolated environment, and a method for sealingly coupling a facility or isolation system to an accessory via a sealing device to form the sealed system. It will be appreciated by those skilled in the art that changes may be made to the embodiments described above without departing from the broad inventive concepts thereof. It is understood, therefore, that this invention is not limited to particular embodiments disclosed, but is intended to cover modifications within the spirit and scope of the present invention as defined by the appended claims.

What is claimed is:

1. A sealed system for handling, manipulating and formulating materials in an isolated environment, the system comprising:

a portable isolation system for performing at least a portion of the handling, manipulating, and formulating, the isolation system having an interior at least partially defined by a plurality of walls, an inlet port for allowing air to flow into the interior, an outlet port for allowing air to flow out of the interior, and a transfer port positioned on one of the walls for transferring items into and out of the isolation system;

an autoclave fixedly mounted to a building wall and selectively coupled to the transfer port of the isolation system and having an interior for receiving the items, the interior being accessible through an opening, the building wall having an opening in registry with the opening of the autoclave;

a substantially outwardly extending trough of predetermined configuration surrounding one of the transfer port of the isolation system and the opening of the autoclave, the trough having a sealing substance disposed therein; and a substantially outwardly extending blade of predetermined configuration surrounding the other of the transfer port of the isolation system and the opening of the autoclave, the configuration of the blade corresponding to the configuration of the trough, the blade being aligned with and placed within the trough such that the blade sealingly engages the sealing substance within the trough to prevent external matter from passing into the interior of the isolation system and the interior of the autoclave through the transfer port and the opening, the interior of the coupled autoclave being accessible from the interior of the isolation system through the transfer port of the isolation system and the opening of the autoclave.

2. The sealed system of claim 1 further comprising a releasable securing device maintaining the blade in sealing engagement with the sealing substance within the trough.

3. The sealed system of claim 2 wherein the securing device comprises a plurality of first securing members spaced around the trough and a corresponding plurality of complementary second securing members spaced around the blade, the first securing members engaging the second securing members to maintain the blade within the trough.

4. The sealed system of claim 1 wherein the sealing substance is a gel.

5. The sealed system of claim 1 wherein the isolation system includes a worker access port for allowing at least a portion of a worker to access the interior of the isolation system.

6. The sealed system of claim 1 wherein the isolation system further comprises wheels to provide the portability.

7. The sealed system of claim 1 wherein the blade surrounds the opening of the autoclave and the trough surrounds the transfer port of the isolation system.

8. The sealed system of claim 7 wherein the blade and the trough each surround and define an inner area, the sealed system further comprising a generally planar mounting member having an aperture in registry with the inner areas of the blade and the trough, the opening of the autoclave, and the transfer port of the isolation system, the blade being sealingly mounted to the mounting member, the mounting member being sealingly mounted to the autoclave for sealing the interior of the autoclave.

9. The sealed system of claim 1 further comprising flow control means for causing air to flow through the inlet port into the interior of the isolation system and out of the interior of the isolation system through the outlet port.

10. A method for sealingly coupling a portable isolation system for handling, manipulating and formulating materials and an autoclave fixedly mounted to a building wall, the method comprising the steps of:
   providing the isolation system having an interior at least partially defined by a plurality of walls and a transfer port positioned on one of the walls;
   providing the autoclave having an interior accessible through an opening, the building wall having an opening in registry with the opening of the autoclave;
   providing a substantially outwardly extending trough of predetermined configuration surrounding one of the transfer port and the opening, the trough having a sealing substance disposed therein;
   providing a substantially outwardly extending blade of predetermined configuration surrounding the other of the transfer port and the opening, the configuration of the blade corresponding to the configuration of the trough;
   positioning the isolation system with respect to the autoclave such that the blade and the trough are proximate one another and in registry; and
   sealingly coupling the blade to the sealing substance within the trough to prevent external matter from passing into the isolation system and the autoclave through the transfer port and the opening, the interior of the coupled autoclave being accessible from the interior of the isolation system through the transfer port and the opening.

11. A sealed system for handling, manipulating and formulating materials in an isolated environment, the system comprising:
   a portable isolation system for performing at least a portion of the handling, manipulating, and formulating, the isolation system having an interior at least partially defined by a plurality of walls, an inlet port for allowing air to flow into the interior, an outlet port for allowing air to flow out of the interior, and a transfer port positioned on one of the walls for transferring items into and out of the isolation system;
   an autoclave for receiving items from the isolation system, sterilizing the items, and returning the items to the isolation system, the autoclave being fixedly mounted to a wall of a building and selectively coupled to the transfer port of the isolation system and having an interior for accepting the items, the interior being accessible through an opening, the opening and transfer port being in registry when the autoclave is coupled with the isolation system, the wall having an opening in registry with the opening of the autoclave; and
   a sealing device interconnecting the isolation system and the autoclave and sealingly engaging the transfer port of the isolation system to the opening of the autoclave to prevent external matter from passing into the interior of the isolation system and the interior of the autoclave through the transfer port and the opening.

12. The sealed system of claim 11 wherein the sealing device comprises:
   a substantially outwardly extending trough of predetermined configuration surrounding one of the transfer port of the isolation system and the opening of the autoclave, the trough having a sealing substance disposed therein; and
   a substantially outwardly extending blade of predetermined configuration surrounding the other of the transfer port of the isolation system and the opening of the autoclave, the configuration of the blade corresponding to the configuration of the trough, the blade being aligned with and placed within the trough such that the blade sealingly engages the sealing substance within the trough to prevent matter from passing therebetween, the interior of the coupled autoclave being accessible from the interior of the isolation system by the transfer port of the isolation system and the opening of the autoclave.

13. The sealed system of claim 12 wherein the blade surrounds the opening of the autoclave and the trough surrounds the transfer port of the isolation system.

14. The sealed system of claim 13 wherein the blade and the trough each surround and define an inner area, the sealed system further comprising a substantially planar mounting member having an aperture in registry with the inner areas of the blade and the trough, the opening of the autoclave, and the transfer port of the isolation system, the blade being sealingly mounted to the mounting member, the mounting member being sealingly mounted to the autoclave for sealing the interior of the autoclave.

15. The sealed system of claim 12 further comprising a releasable securing device for maintaining the blade in sealing engagement with the sealing substance within the trough.

16. The sealed system of claim 15 wherein the securing device comprises a plurality of first securing members spaced around the trough and a corresponding plurality of complementary second securing members spaced around the blade, the first securing members engaging the second securing members to maintain the blade within the trough.

17. The sealed system of claim 12 wherein the sealing substance is a gel.

18. The sealed system of claim 11 wherein the isolation system further comprises wheels to provide the portability.

19. The sealed system of claim 11 wherein the isolation system includes a worker access port for allowing at least a portion of a worker to access the interior of the isolation system.

20. The sealed system of claim 11 further comprising flow control means for causing air to flow through the inlet port into the interior of the isolation system and out of the interior of the isolation system through the outlet port.

* * * * *